(12) United States Patent
Bos et al.

(10) Patent No.: US 10,329,222 B2
(45) Date of Patent: *Jun. 25, 2019

(54) ALKANE OXIDATIVE DEHYDROGENATION

(71) Applicant: SHELL OIL COMPANY, Houston, TX (US)

(72) Inventors: Alouisius Nicolaas Renée Bos, Amsterdam (NL); Georgios Mitkidis, Amsterdam (NL); Guus Van Rossum, Amsterdam (NL); Maria San Roman Macia, Amsterdam (NL); Ronald Jan Schoonebeek, Amsterdam (NL); Vatsal Mukundlal Shah, Sugar Land, TX (US); Michael Johannes Franciscus Maria Verhaak, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/760,272

(22) PCT Filed: Sep. 16, 2016

(86) PCT No.: PCT/EP2016/071948
§ 371 (c)(1),
(2) Date: Mar. 15, 2018

(87) PCT Pub. No.: WO2017/046315
PCT Pub. Date: Mar. 23, 2017

(65) Prior Publication Data
US 2018/0258012 A1    Sep. 13, 2018

(30) Foreign Application Priority Data
Sep. 18, 2015  (EP) .................... 15185778

(51) Int. Cl.
*C07C 5/48*       (2006.01)
*C07C 11/04*      (2006.01)
(Continued)

(52) U.S. Cl.
CPC .............. *C07C 5/48* (2013.01); *B01J 27/0576* (2013.01); *C07D 301/08* (2013.01);
(Continued)

(58) Field of Classification Search
CPC .. C07C 2/84; C07C 5/48; C07C 7/152; C07C 11/02; C07D 301/08; C07D 303/00
See application file for complete search history.

(56) References Cited

U.S. PATENT DOCUMENTS 4,524,236 A † 6/1985 McCain
5,430,181 A * 7/1995 Arpentinier ............. C07B 33/00
549/248

(Continued)

FOREIGN PATENT DOCUMENTS

EP  0 261 264   †  8/1991
GB  1314613 A      4/1973
(Continued)

OTHER PUBLICATIONS

Pilar et al., high ethylene production through oxidative dehydrogenation of ethane, (Chemcat Chem 2011, 3, 1503-1508).*
(Continued)

*Primary Examiner* — Jafar F Parsa

(57) ABSTRACT

The invention relates to a process of the oxidative dehydrogenation of a C2-6 alkane, comprising subjecting a stream comprising methane and the C2-6 alkane, in which stream the volume ratio of methane to the C2-6 alkane is of from 0.005:1 to 100:1, to oxydehydrogenation conditions resulting in a stream comprising methane, a C2-6 alkene and optionally a C2-6 carboxylic acid.

5 Claims, 1 Drawing Sheet

(51) Int. Cl.
 *B01J 27/057* (2006.01)
 *C07D 301/08* (2006.01)
(52) U.S. Cl.
 CPC ...... *C07C 2523/20* (2013.01); *C07C 2523/28* (2013.01); *C07C 2527/057* (2013.01); *Y02P 20/52* (2015.11)

(56) References Cited

U.S. PATENT DOCUMENTS

| | | | |
|---|---|---|---|
| 6,518,476 B1 * | 2/2003 | Culp | C07C 2/84 585/655 |
| 7,091,377 B2 | 8/2006 | Borgmeier et al. | |
| 8,524,927 B2 † | 9/2013 | Mazanec | |
| 2004/0147393 A1 | 7/2004 | Hibst et al. | |
| 2009/0281345 A1 | 11/2009 | Matusz | |
| 2010/0256432 A1 | 10/2010 | Arnold et al. | |

FOREIGN PATENT DOCUMENTS

| | | |
|---|---|---|
| WO | 03064035 A1 | 8/2003 |
| WO | 2010096909 A1 | 9/2010 |
| WO | 2012101069 A1 | 8/2012 |
| WO | 2012101092 A1 | 8/2012 |
| WO | 2012118888 A2 | 9/2012 |
| WO | 2015057753 A1 | 4/2015 |

OTHER PUBLICATIONS

International Search Report and Written Opinion received for PCT Patent Application No. PCT/EP2016/071948, dated Nov. 21, 2016, 8 pages.
Lobera et al., "High Ethylene Production through Oxidative Dehydrogenation of Ethane Membrane Reactors Based on Fast Oxygen-Ion Conductors", ChemCatChem, 2011, 3, 1503-1508; with Supporting Information (2011) retrieved from: https://onlinelibrary.wiley.com/action/downloadSupplement?doi=10.1002%2Fcctc.201100055&file=cctc_201100055_sm_miscellaneous_information.pdf.†
Chevron Phillips Chemical Pipeline Co., LLC, "T.R.S. No. 38", Chevron Pipe Line Co. LLC, Jul. 1, 2012, pp. 1-10.†

* cited by examiner
† cited by third party

ALKANE OXIDATIVE DEHYDROGENATION

PRIORITY CLAIM

The present application is the National Stage (§ 371) of International Application No. PCT/EP2016/071948, filed 16 Sep 2016, which claims priority from European Application No. 15185778.6, filed 18 Sep. 2015 incorporated herein by reference.

FIELD OF THE INVENTION

The present invention relates to a process of alkane oxidative dehydrogenation (oxydehydrogenation; ODH).

BACKGROUND OF THE INVENTION

It is known to oxidatively dehydrogenate alkanes, such as alkanes containing 2 to 6 carbon atoms (C2-6 alkanes), for example ethane or propane resulting in ethylene and propylene (C2-6 alkenes), respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as oxydehydrogenation catalysts.

It is an objective of the present invention to provide an alkane ODH process, which process is performed such that a relatively high conversion, including a high productivity, of a C2-6 alkane into the corresponding C2-6 alkene is obtained.

SUMMARY OF THE INVENTION

It was found that the above-mentioned objective can be obtained by means of an alkane ODH process, wherein a stream comprising methane and the C2-6 alkane, in which stream the volume ratio of methane to the C2-6 alkane is of from 0.005:1 to 100:1, is subjected to oxydehydrogenation conditions resulting in a stream comprising methane, a C2-6 alkene and optionally a C2-6 carboxylic acid.

Accordingly, the present invention relates to a process of the oxidative dehydrogenation of a C2-6 alkane, comprising subjecting a stream comprising methane and the C2-6 alkane, in which stream the volume ratio of methane to the C2-6 alkane is of from 0.005:1 to 100:1, to oxydehydrogenation conditions resulting in a stream comprising methane, a C2-6 alkene and optionally a C2-6 carboxylic acid.

DETAILED DESCRIPTION OF THE INVENTION

Figure 1:
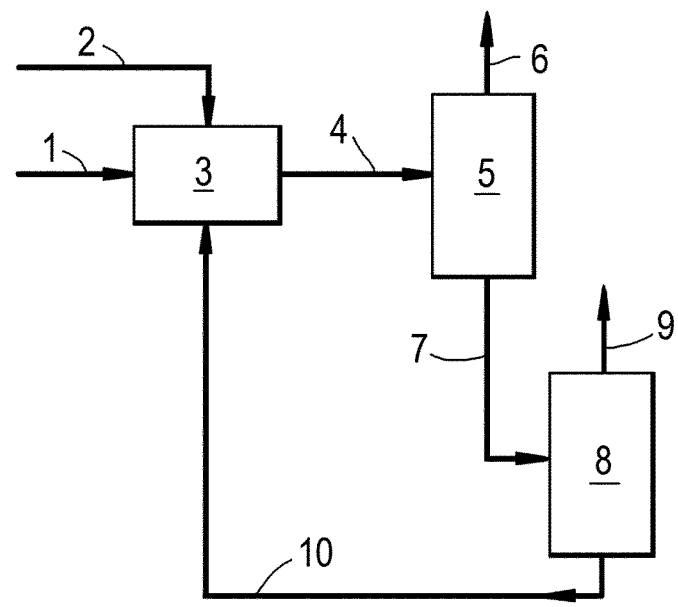
FIG. 1 shows an embodiment of the present invention wherein methane is separated from a stream resulting from the oxydehydrogenation.

Within the present specification, a "C2-6 alkane" refers to an alkane containing 2 to 6 carbon atoms, a "C2-6 alkene" refers to an alkene containing 2 to 6 carbon atoms, and a "C2-6 carboxylic acid" refers to a carboxylic acid containing 2 to 6 carbon atoms.

In the context of the present invention, in a case where a stream, catalyst or composition comprises two or more components, these components are to be selected in an overall amount not to exceed 100%.

While the processes of the present invention and the streams, catalysts or compositions used in said processes are described in terms of "comprising", "containing" or "including" one or more various described steps and components, respectively, they can also "consist essentially of" or "consist of" said one or more various described steps and components, respectively.".

WO2012118888 discloses a process comprising selectively extracting at least one natural gas component from a natural gas stream, which at least one natural gas component may be ethane, by (a) contacting the natural gas stream with a catalyst under conditions that selectively convert the natural gas component into at least one product and (b) separating the product from the remaining components of the natural gas stream. In the present invention, the volume ratio of methane to the C2-6 alkane in the stream comprising methane and the C2-6 alkane which is subjected to oxy-dehydrogenation conditions, is of from 0.005:1 to 100:1. Preferably, said volume ratio of methane to the C2-6 alkane is of from 0.2:1 to 100:1, more preferably of from 0.5:1 to 100:1, more preferably 1:1 to 50:1, more preferably 1.5:1 to 30:1, more preferably 2:1 to 20:1, most preferably 3:1 to 10:1. Further, said volume ratio of methane to the C2-6 alkane is at least 0.005:1, or may be at least 0.2:1 or at least 0.3:1 or at least 0.4:1 or at least 0.5:1 or at least 1:1 or at least 1.5:1 or at least 2:1 or at least 2.5:1 or at least 3:1. Still further, said volume ratio of methane to the C2-6 alkane is at most 100:1, or may be at most 70:1 or at most 50:1 or at most 30:1 or at most 20:1 or at most 10:1 or at most 8:1 or at most 7:1 or at most 6:1 or at most 5:1 or at most 4.8:1 or at most 4.5:1 or at most 4:1. In particular, said volume ratio of methane to the C2-6 alkane may be of from 0.005:1 to 4.8:1.

Said ratio of methane to the C2-6 alkane is the ratio at the entrance of a reactor, which reactor may comprise a catalyst bed. Obviously, after entering the reactor, at least part of the C2-6 alkane gets converted.

It has been found that in the presence of methane in said volume ratio of methane to the C2-6 alkane, a relatively high conversion of the C2-6 alkane into the corresponding C2-6 alkene and the optional corresponding C2-6 carboxylic acid, including a high productivity, is obtained in an alkane ODH process. More in particular, in the present invention, a relatively high oxygen to C2-6 alkane volume ratio may be applied, as further described below. That is, the presence of methane makes it possible to employ a relatively high oxygen to C2-6 alkane volume ratio, while staying in the non-flammability region, so as to convert as much C2-6 alkane as possible under safe conditions. Additionally, the dilution of the feed to the alkane ODH process by methane, thereby making the C2-6 alkane concentration relatively low, results in good dissipation of the exothermic heat generated by the alkane ODH process.

Advantageously, through the relatively high conversion, including a high productivity, the present invention enables the use of a simpler separation section in the production of a C2-6 alkene by alkane oxydehydrogenation. For because of the elevated conversion, including an elevated productivity, no separate splitter for splitting C2-6 alkane from C2-6 alkene would be required while generating said alkene with only a low content of the starting alkane. Suitably, such relatively pure alkene can then be easily further converted into other chemical products. In the alkane oxidative dehydrogenation process of the present invention, the conversion of the C2-6 alkane, as fed to a reactor, may vary widely. Suitably, said conversion is higher than 30%, or of from 35 to 95%, or of from 40 to 70%, or of from 45 to 55%. Suitably, said conversion is higher than 30%, more suitably at least 35%, more suitably at least 40%, most suitably at least 45%. Further, suitably, said conversion is at most 95%, more suitably at most 85%, more suitably at most 75%, more suitably at most 70%, more suitably at most 65%, more suitably at most 60%, most suitably at most 55%. By said "conversion", reference is made to a "conversion per pass" in the case of a reactor where unconverted reactant(s) is (are) recovered from the product stream and recycled to the reactor.

Preferably, in the alkane oxidative dehydrogenation process of the present invention, the C2-6 alkane is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the C2-6 alkane is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The present alkane oxidative dehydrogenation process may comprise contacting a gas stream comprising oxygen ($O_2$), methane and the C2-6 alkane with a catalyst. Said oxygen is an oxidizing agent, thereby resulting in oxidative dehydrogenation of the alkane. Said oxygen may originate from any source, such as for example air. Thus, in the present invention, oxygen may be provided by introducing high-purity oxygen or air into the process. High-purity oxygen may have a purity greater than 90%, preferably greater than 95%, more preferably greater than 99%, and most preferably greater than 99.4%.

In the present invention, one gas stream comprising oxygen, methane and the C2-6 alkane may be fed to a reactor. Alternatively, two or more gas streams may be fed to the reactor, which gas streams form a combined gas stream inside the reactor. For example, one gas stream comprising oxygen and another gas stream comprising methane and the C2-6 alkane, such as ethane, may be fed to the reactor separately.

An advantage of using a stream comprising methane and a C2-6 alkane in the present process is that because of the positive effect of the presence of methane on the conversion, including productivity, of a C2-6 alkane in an alkane ODH process, as demonstrated by the present invention, no prior separation of methane from the C2-6 alkane is needed which results in substantial savings on capital expenditure.

It is envisaged by the present inventors that in the present invention, the stream comprising methane and the C2-6 alkane, preferably ethane and/or propane, to be subjected to oxydehydrogenation conditions is provided by a plant which produces such stream, for example as a sidestream, such as a natural gas production plant, shale gas production plant, natural gas processing plant, Natural Gas Liquids (NGL) recovery and fractionation plant, Liquefied Natural Gas (LNG) production plant and so on, which plants may also be generally referred to as so-called "midstream" plants. Therefore, the present process may be integrated with any one of such midstream plants. However, in the present invention, it is not essential how the stream comprising methane and the C2-6 alkane, preferably ethane and/or propane, to be subjected to oxydehydrogenation conditions, has been produced.

In addition to methane and C2-6 alkane, said one gas stream or multiple gas streams may additionally comprise an inert gas selected from the group consisting of the noble gases and nitrogen ($N_2$). Preferably, such additional inert gas is nitrogen or argon, more preferably nitrogen. A further advantage of the present invention is that because of the presence of methane, no such additional inert gas needs to be added or only a substantially smaller amount. If such additional inert gas is nitrogen, such nitrogen preferably originates from any air used as source of the oxidizing agent (oxygen).

Ranges for the volume ratio of oxygen to the C2-6 alkane in the gas stream comprising oxygen, methane and the C2-6 alkane which in the present invention are suitable, depend on whether or not a C2-6 alkene or a C2-6 carboxylic acid is desired as a main product. For in a case where a C2-6 carboxylic acid is desired as a main product, a relatively higher amount of oxygen is required. The presence of and amount of double bonds in the C2-6 alkene and C2-6 carboxylic acid products also determine the amount of oxygen needed. Generally, in the present invention, said volume ratio of oxygen to the C2-6 alkane may be in the range of from 0.1:1 to 10:1, more suitably 0.3:1 to 7:1, most suitably 0.5:1 to 5:1.

Said ratio of oxygen to the C2-6 alkane is the ratio at the entrance of a reactor, which reactor may comprise a catalyst bed. Obviously, after entering the reactor, at least part of the oxygen and C2-6 alkane gets converted.

As mentioned above, in the present invention, a gas stream comprising oxygen, methane and the C2-6 alkane may be contacted with a catalyst. The amount of such catalyst is not essential. Preferably, a catalytically effective amount of the catalyst is used, that is to say an amount sufficient to promote the alkane oxydehydrogenation reaction.

Further, in the present invention, such catalyst may be a mixed metal oxide catalyst containing molybdenum, vanadium, niobium and optionally tellurium as the metals. Thus, in a preferred embodiment of the present invention, the stream comprising methane and the C2-6 alkane, in which stream the volume ratio of methane to the C2-6 alkane is of from 0.005:1 to 100:1, is subjected to oxydehydrogenation conditions by contacting a gas stream comprising comprising oxygen, methane and the C2-6 alkane with a mixed metal oxide catalyst containing molybdenum, vanadium, niobium and optionally tellurium, resulting in the stream comprising methane and the C2-6 alkene.

In the present invention, the above-mentioned mixed metal oxide catalyst containing molybdenum, vanadium, niobium and optionally tellurium may have the following formula:

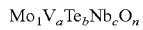
$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

In the present invention, the above-mentioned mixed metal oxide catalyst containing molybdenum, vanadium, niobium and optionally tellurium is a solid, heterogeneous catalyst. Inside a reactor, this heterogeneous catalyst makes up a catalyst bed through which the gas stream comprising oxygen, methane and the C2-6 alkane is sent.

In the alkane oxidative dehydrogenation process of the present invention, typical pressures are 1 to 50 bara (i.e. "bar absolute"), suitably 5 to 25 bara, and typical temperatures (catalyst operating temperature or catalyst bed temperature) are 100-600° C., suitably 200-500° C. Advantageously, in the present invention, a relatively high pressure, up to 50 or 25 bara, may be applied which results in smaller volumes and less compression needs.

In general, the product stream comprises water in addition to the desired product. Water may easily be separated from said product stream, for example by cooling down the product stream from the reaction temperature to a lower temperature, for example room temperature, so that the water condenses and can then be separated from the product stream. In case any carboxylic acid is formed in the present alkane ODH process, such as the above-mentioned acetic acid and acrylic acid, such carboxylic acid would be separated at the same time together with the water. In a preferred embodiment, wherein the stream resulting from the present alkane ODH process comprises methane, a C2-6 alkene, water and optionally a C2-6 carboxylic acid, said water and optional C2-6 carboxylic acid are preferably removed from said stream by subjecting said stream to a condensation treatment, for example by cooling down said stream to a temperature in the range of from 0 to 50° C., suitably 10 to 40° C. or 10 to 30° C.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

The stream resulting from the oxydehydrogenation in the process of the present invention, which comprises methane, a C2-6 alkene and optionally a C2-6 carboxylic acid, may additionally comprise unconverted C2-6 alkane.

In a preferred embodiment of the present invention, methane is separated from the stream comprising methane, the C2-6 alkene and the optional C2-6 carboxylic acid, resulting from the oxydehydrogenation, preferably after removing any water and C2-6 carboxylic acid as described above. The methane may be separated by means of distillation. Said preferred embodiment is shown in FIG. 1.

In the flow scheme of FIG. 1, stream 1 comprising methane and ethane is fed to oxydehydrogenation unit 3. Stream 2 comprising an oxidizing agent, for example in the form of air, is also fed to oxydehydrogenation unit 3. Stream 4 comprising methane, ethylene and unconverted ethane leaving oxydehydrogenation unit 3 is fed to distillation column 5. Stream 4 also comprises water and optionally acetic acid which are removed in a water separation unit (not shown in FIG. 1). Optionally, stream 4 may also comprise carbon dioxide which may be removed in a carbon dioxide removal unit (not shown in FIG. 1) before stream 4 is sent to distillation column 5. A top stream 6 comprising methane leaves distillation column 5. Further, bottom stream 7 comprising ethylene and ethane leaves distillation column 5 and is sent to distillation column 8. Optionally, a third stream (not shown in FIG. 1) may be separated in distillation column 5, namely a top bleed stream comprising uncondensable components, such as oxygen. A top stream 9 comprising ethylene leaves distillation column 8. Further, bottom stream 10 comprising ethane leaves distillation column 8 and is recycled to oxydehydrogenation unit 3.

In another preferred embodiment of the present invention, C2-6 alkene from the stream comprising methane, the C2-6 alkene and the optional C2-6 carboxylic acid, resulting from the oxydehydrogenation, is converted into another chemical product, preferably after removing any water and C2-6 carboxylic acid as described above. In a case where the C2-6 alkane is ethane and the C2-6 alkene is ethylene, ethylene may be converted into ethylene oxide. Further, in a case where the C2-6 alkane is propane and the C2-6 alkene is propylene, propylene may be converted into acrylic acid. Other envisaged conversions of ethylene are: 1) reaction of ethylene and benzene into ethylbenzene (EB); 2) oligomerization or polymerization of ethylene into for example polyethylene (PE); 3) conversion of ethylene into aromatics, such as benzene, toluene and xylenes (BTX); 4) reaction of ethylene and acetic acid into vinylacetate.

In the above-mentioned other preferred embodiment of the present invention, part of the methane may be separated before C2-6 alkene is converted into another chemical product. The methane may be separated by means of distillation.

The stream resulting from the above-mentioned step wherein C2-6 alkene is converted into another chemical product, which stream comprises said chemical product and methane, may additionally comprise unconverted C2-6 alkane and/or unconverted C2-6 alkene.

Further, in the above-mentioned other preferred embodiment of the present invention, wherein ethylene is converted into ethylene oxide, preferably, the present process comprises subjecting a stream comprising methane and ethane, in which stream the volume ratio of methane to ethane is of from 0.005:1 to 100:1, to oxydehydrogenation conditions resulting in a stream comprising methane, ethylene and optionally acetic acid;

subjecting ethylene and methane from the stream comprising methane, ethylene and optionally acetic acid to oxidation conditions resulting in a stream comprising ethylene oxide and methane; and recovering ethylene oxide from the stream comprising ethylene oxide and methane.

Accordingly, the present invention also relates to a process for the production of ethylene oxide, comprising subjecting a stream comprising methane and ethane, in which stream the volume ratio of methane to ethane is of from 0.005:1 to 100:1, to oxydehydrogenation conditions resulting in a stream comprising methane, ethylene and optionally acetic acid;

subjecting ethylene and methane from the stream comprising methane, ethylene and optionally acetic acid to oxidation conditions resulting in a stream comprising ethylene oxide and methane; and recovering ethylene oxide from the stream comprising ethylene oxide and methane.

In the above-mentioned process, ethylene oxide is produced from ethylene that was produced by oxidative dehydrogenation of ethane. In general, in such case before a subsequent step wherein the ethylene is further converted into a useful chemical intermediate, such as ethylene oxide, the ethylene containing product stream produced in the oxidative dehydrogenation of ethane has to be purified. For example, in the above-mentioned process, the oxydehydrogenation step results in a stream comprising methane, ethylene and optionally unconverted ethane. In order to prevent any interference of methane and any unconverted ethane, the ethylene containing product stream would generally be freed from methane and any unconverted ethane, so that a purified ethylene stream would be fed to the subsequent step of ethylene oxide production. However, having to separate methane and any unconverted ethane from the ethylene is very cumbersome and results in a high expenditure for producing ethylene and relatively high ethylene losses.

Further, in the above-mentioned ethylene oxide production process, a ballast gas would have to be added. For in the oxidation of ethylene an oxidizing agent, such as high-purity oxygen or air, is required. Because an oxidizing agent is required, it is important to control the safe operability of the reaction mixture. Nitrogen may be utilized as such ballast gas. One function of a ballast gas is thus to control this safe operability. It is very cumbersome to provide such ballast gas and feed it to the ethylene oxidation unit, which results in a high expenditure for producing ethylene oxide.

An advantage of the above-mentioned process, wherein ethylene oxide is produced from ethylene that was produced by oxidative dehydrogenation of ethane from a feed containing methane and ethane, is that no methane and no unconverted ethane (if any) have to be separated from the ethylene containing product stream that results from the oxydehydrogenation step. This results in a much simpler overall process using less separation processes and equipment. In addition, the non-separated methane and unconverted ethane (if any) advantageously function as ballast gases in the next ethylene oxidation step so that no or substantially less additional ballast gas, such as nitrogen, needs to be added. This results in a much simpler and more efficient ethylene oxidation process. Still further, separation of the stream comprising methane, ethylene and unconverted ethane (if any) resulting from the oxydehydrogenation step of the above-mentioned process is advantageously automatically, and at least partially, effected in the ethylene oxide production step wherein the ethylene is converted into ethylene oxide which can be separated more easily from the non-converted methane and unconverted ethane (if any). All these and other advantages result in a substantial reduction of expenditure, for example savings on costs for compression, refrigeration, etc. needed for separating methane and any unconverted ethane from the ethylene.

In the above-mentioned ethylene oxide production process, the step of subjecting the stream comprising methane and ethane, in which stream the volume ratio of methane to ethane is of from 0.005:1 to 100:1, to oxydehydrogenation conditions resulting in a stream comprising methane, ethylene and optionally acetic acid, may be performed in the same way as described above in general for a stream comprising methane and a C2-6 alkane.

Further, the stream resulting from the oxydehydrogenation step in the above-mentioned ethylene oxide production process, which stream may comprise methane, ethylene, water and optionally acetic acid, may be subjected to a condensation treatment as described above in general for a stream comprising methane, a C2-6 alkane, water and optionally a C2-6 carboxylic acid, such as to remove water and any acetic acid therefrom.

Still further, as already referred to above, between the above-mentioned oxydehydrogenation and oxidation steps, part of the methane may be separated, for example by means of distillation, preferably after having removed any water and acetic acid. However, advantageously, in the above-mentioned ethylene oxide production process, such methane separation step may be omitted.

The stream resulting from the above-mentioned ethylene oxidation step which comprises ethylene oxide and methane, may additionally comprise unconverted ethane and/or unconverted ethylene.

The ethylene oxidation step in the above-mentioned process results in a stream comprising ethylene oxide, methane, optionally unconverted ethylene and optionally unconverted ethane from the preceding oxydehydrogenation step. The ethylene oxide can be recovered easily from such stream by means of methods known to the skilled person. That is to say, ethylene oxide may be separated from said stream resulting in a stream comprising methane, optionally unconverted ethylene and optionally unconverted ethane. Any unconverted ethylene and ethane from the latter stream may be recycled and advantageously be converted and re-used, respectively, after such recycle. After ethylene oxide is separated from said stream and before such recycle of the remaining unconverted ethylene and ethane, any carbon dioxide may be removed. That is to say, either part or all carbon dioxide is removed. Said carbon dioxide may be produced in the ethylene oxide production step and/or may be produced in the oxydehydrogenation step. Ways of removing carbon dioxide, such as a caustic or amine wash, are known to the skilled person. Another advantage of the above-mentioned process is that any carbon dioxide produced in the oxydehydrogenation step does not have to be removed before the ethylene oxidation step. Such carbon dioxide removal can be postponed till after said ethylene oxidation step.

Any unconverted ethylene and optionally any unconverted ethane, from the stream resulting from the step of producing ethylene oxide may be partially or completely recycled to that step of producing ethylene oxide. The recycled unconverted ethylene is then advantageously converted as yet in that ethylene oxidation step. Further, any recycled unconverted ethane is then advantageously re-used as a ballast gas in that ethylene oxidation step. In this embodiment, a stream comprising any unconverted ethylene and optionally any unconverted ethane is separated from the stream resulting from the step of producing ethylene oxide, and is then recycled to the step of producing ethylene oxide. Such recycle has both said advantages in that conversion of unconverted ethylene into ethylene oxide is effected as yet, whereas re-use of any unconverted ethane as a ballast gas is also effected at the same time.

In the above-mentioned process, the stream resulting from the step of producing ethylene oxide may be separated into a stream comprising methane and a stream comprising any unconverted ethane and any unconverted ethylene. The latter stream comprising any unconverted ethane and any unconverted ethylene may then be partially or completely recycled to the step of producing ethylene oxide. Still further, said stream comprising any unconverted ethane and any unconverted ethylene may be separated into a stream comprising any unconverted ethylene and a stream comprising any unconverted ethane. Said stream comprising any unconverted ethylene may be recycled to the step of producing ethylene oxide. Said stream comprising any unconverted ethane may be recycled to the oxydehydrogenation step, as further discussed below. The latter separation, advantageously, is not critical so that a complete separation of ethane from ethylene is not needed. For ethane is both starting material in the oxydehydrogenation step and ballast gas in the subsequent ethylene oxide production step. For example, all that matters is that the separated substream which comprises more ethylene than the other separated substream, which comprises ethane, is recycled to the step of producing ethylene oxide, whereas the other separated substream is recycled to the oxydehydrogenation step.

Any unconverted ethane from the stream resulting from the step of producing ethylene oxide may be partially or completely recycled to the oxydehydrogenation step. This embodiment has the advantage that more ethylene may be produced by recycling unconverted ethane whereas ethane that is still not converted after such recycle will then automatically be re-used as a ballast gas in the ethylene oxidation step. Such recycle of unconverted ethane to the oxydehydrogenation step may be performed in many ways. One example has been described above.

Further, any unconverted ethane from the stream comprising resulting from the step of producing ethylene oxide may also be recycled to both the oxydehydrogenation step and the ethylene oxide production step.

In the ethylene oxide production step of the above-mentioned process, methane, ethylene and any unconverted ethane from the stream resulting from the oxydehydrogenation step are contacted with an oxidizing agent, for example in the form of high-purity oxygen or air, preferably high-purity oxygen which may have a purity greater than 90%, preferably greater than 95%, more preferably greater than 99%, and most preferably greater than 99.4%. Typical reaction pressures are 1-40 bar, suitably 10-30 bar, and typical reaction temperatures are 100-400° C., suitably 200-300° C.

An additional advantage of the above-mentioned process is that there is no need to remove remaining oxidizing agent, if any, from the product stream resulting from the oxydehydrogenation step, because oxidizing agent is needed any way in the subsequent production of ethylene oxide. For it is cumbersome to eliminate unreacted oxygen from an ethane oxydehydrogenation product stream.

Further, advantageously, the same source of oxidizing agent as used for feeding oxidizing agent to the ethylene oxide production step of the above-mentioned process, can be used for feeding oxidizing agent to the ethane oxydehydrogenation step of that same process.

Further, it is preferred that in the ethylene oxide production step of the above-mentioned process, the methane, ethylene and any unconverted ethane are contacted with a catalyst, preferably a silver containing catalyst. A typical reactor for the ethylene oxide production step consists of an assembly of tubes that are packed with catalyst. A coolant may surround the reactor tubes, removing the reaction heat and permitting temperature control.

In case a silver containing catalyst is used in the ethylene oxide production step of the above-mentioned process, the silver in the silver containing catalyst is preferably in the form of silver oxide. Preferred is a catalyst comprising particles wherein silver is deposited on a carrier. Suitable carrier materials include refractory materials, such as alumina, magnesia, zirconia, silica and mixtures thereof. The catalyst may also contain a promoter component, e.g. rhenium, tungsten, molybdenum, chromium, nitrate- or nitrite-forming compounds and combinations thereof. Preferably, the catalyst is a pelletized catalyst, for example in the form of a fixed catalyst bed, or a powdered catalyst, for example in the form of a fluidized catalyst bed.

The nature of the ethylene oxidation catalyst, if any, is not essential in terms of obtaining the advantages of the present invention as described herein. The amount of the ethylene oxidation catalyst is neither essential. If a catalyst is used, preferably a catalytically effective amount of the catalyst is used, that is to say an amount sufficient to promote the ethylene oxidation reaction.

Examples of ethylene oxidation processes, including catalysts and other process conditions, are for example disclosed in US20090281345 and GB1314613, the disclosures of which are herein incorporated by reference. All of these ethylene oxidation processes are suitable for the ethylene oxidation step of the above-mentioned process.

Figure 2:
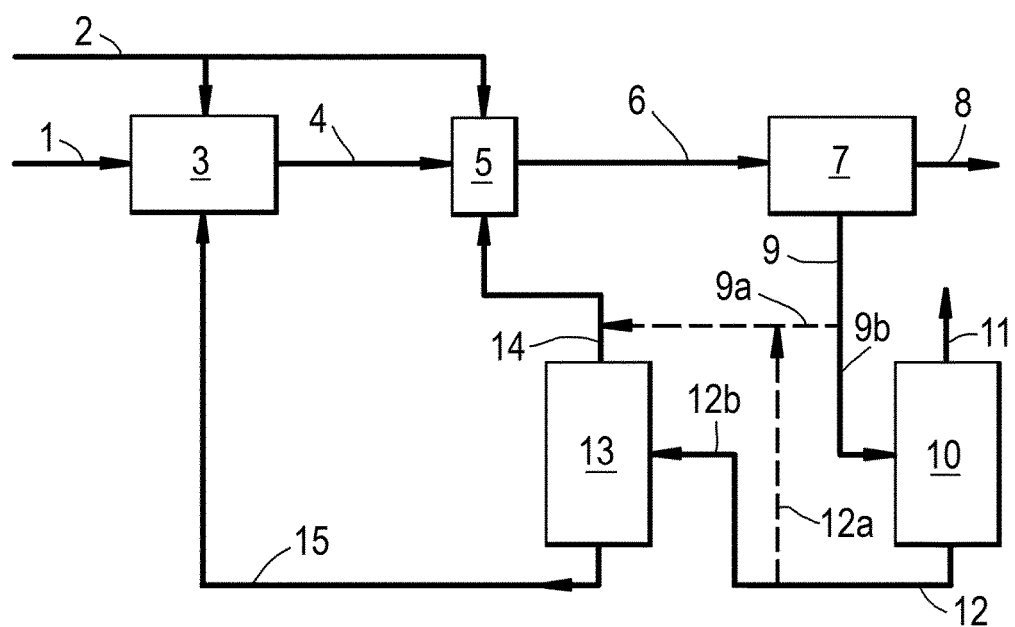
FIG. 2 shows an embodiment of the present invention wherein ethylene from a stream resulting from the oxydehydrogenation, is converted into ethylene oxide.

The above-mentioned other preferred embodiment of the present invention, wherein ethylene is converted into ethylene oxide, is shown in FIG. 2.

In the flow scheme of FIG. 2, stream 1 comprising methane and ethane is fed to oxydehydrogenation unit 3. Stream 2 comprising an oxidizing agent, for example in the form of air, is also fed to oxydehydrogenation unit 3. Stream 4 comprising methane, ethylene and unconverted ethane leaving oxydehydrogenation unit 3 is fed to ethylene oxide production unit 5. Stream 4 also comprises water and optionally acetic acid which are removed in a water separation unit (not shown in FIG. 2). Optionally, stream 4 is subjected to hydrotreatment in a hydrotreater unit (not shown in FIG. 2) to convert any acetylene present, before entering ethylene oxide production unit 5. Further, stream 2 comprising an oxidizing agent, for example in the form of air, is fed to ethylene oxide production unit 5. Stream 6 comprising ethylene oxide, methane, unconverted ethylene and unconverted ethane leaving ethylene oxide production unit 5 is sent to ethylene oxide separation unit 7. Ethylene oxide is recovered via stream 8 leaving ethylene oxide separation unit 7. Stream 9 comprising methane, unconverted ethylene and unconverted ethane leaving ethylene oxide separation unit 7 is sent to distillation column 10. Optionally, stream 9 is split into two substreams 9a and 9b, wherein substream 9a is recycled to ethylene oxide production unit 5 and substream 9b is sent to distillation column 10. Further, optionally, stream 9 may also comprise carbon dioxide which may be removed in a carbon dioxide removal unit (not shown in FIG. 2) before stream 9 is sent to distillation column 10 and before stream 9 is optionally split. A top stream 11 comprising methane leaves distillation column 10. Further, bottom stream 12 comprising ethylene and ethane leaves distillation column 10 and is sent to distillation column 13. Optionally, a third stream (not shown in FIG. 2) may be separated in distillation column 10, namely a top bleed stream comprising uncondensable components, such as oxygen. Further, optionally, stream 12 is split into two substreams 12a and 12b, wherein substream 12a is recycled to ethylene oxide production unit 5 and substream 12b is sent to distillation column 13. A top stream 14 comprising ethylene leaves distillation column 13 and is recycled to ethylene oxide production unit 5. Further, bottom stream 15 comprising ethane leaves distillation column 13 and is recycled to oxydehydrogenation unit 3.

The invention is further illustrated by the following Examples.

EXAMPLES (A) Preparation of the Catalyst

A mixed metal oxide catalyst containing molybdenum (Mo), vanadium (V), niobium (Nb) and tellurium (Te) was prepared, for which catalyst the volume ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was evaporated to dryness with the aid of a rotating evaporator ("rotavap") at 50° C.

The dried material was further dried in static air at 120° C. for 16 hours, milled to a fine powder and then calcined in static air at a temperature of 300° C. for 5 hours. After the air calcination, the material was further calcined in a nitrogen ($N_2$) stream at 600° C. for 2 hours. Then the material was treated with an aqueous 5% oxalic acid solution at 80° C. and filtered and dried at 120° C.

The dried catalyst powder was pressed into pills which pills were then milled. The milled material was then sieved using a sieve having a mesh size of 40-80 mesh. The sieved material having a size of 40-80 mesh was then used in the ethane oxidative dehydrogenation experiments described below.

(B) Catalytic Oxidative Dehydrogenation of Ethane

The catalyst thus prepared was used in experiments involving ethane oxidative dehydrogenation within a small-scale testing unit comprising a vertically oriented, cylindrical, quartz reactor having an inner diameter of 3 mm. 1218 mg of the catalyst were loaded in the reactor.

In the experiments, a gas stream comprising ethane ($C_2H_6$), oxygen ($O_2$), methane ($CH_4$) and nitrogen ($N_2$) was fed to the top of the reactor and then sent downwardly through the catalyst bed to the bottom of the reactor. Said gas stream was a combined gas stream comprising a flow of ethane, a flow of oxygen, a flow of methane and a flow of nitrogen having a combined total flow rate of 6 Nl/hr. "Nl" stands for "normal liter" as measured at standard temperature and pressure, namely 32° F. (0° C.) and 1 bara (100 kPa). The catalyst bed temperature (or catalyst operating temperature) was 292° C. The total pressure in the reactor was 3 bara. The gas hourly space velocity was 8230 Nl/hr/lt catalyst. The individual flow rates for nitrogen, oxygen, methane and ethane, and the volume ratios of methane to ethane in the feedstream, are shown in Table 1 below.

TABLE 1

| Exp. | Flow $N_2$ (Nl/hr) | Flow $O_2$ (Nl/hr) | Flow $CH_4$ (Nl/hr) | Flow $C_2H_6$ (Nl/hr) | Volume ratio $CH_4:C_2H_6$ |
|---|---|---|---|---|---|
| 1 | 0.1 | 0.7 | 3.1 | 2.1 | 1.5:1 |
| 2 | 0.1 | 0.4 | 4.1 | 1.4 | 2.9:1 |
| 3 | 0.1 | 0.2 | 5.0 | 0.7 | 7.1:1 |

The conversion of ethane, the conversion of oxygen and the product composition were measured with a gas chromatograph (GC) equipped with a thermal conductivity detector (TCD) and with another GC equipped with a flame ionization detector. The water and any acetic acid from the reaction were trapped in a quench pot. In Table 2 below, the experimental results are shown, including the conversion of ethane, the conversion of oxygen and the space-time yield (STY). The STY represents the productivity that was achieved (in grams of ethylene per hour per liter of catalyst).

TABLE 2

| Exp. | Conversion of oxygen (%) | Conversion of ethane (%) | STY (g $C_2H_4$/hr/lt catalyst) |
|---|---|---|---|
| 1 | 7.3 | 3.3 | 100 |
| 2 | 7.5 | 3.2 | 65 |
| 3 | 6.5 | 3.0 | 34 |

That which is claimed is:

1. A process of the oxidative dehydrogenation of a C2-6 alkane, comprising subjecting a stream comprising methane and the C2-6 alkane, in which stream the volume ratio of methane to the C2-6 alkane is from 0.005:1 to 100:1 to oxydehydrogenation conditions by contacting the stream with a mixed metal oxide catalyst containing molybdenum, vanadium, niobium, and optionally tellurium, resulting in a stream comprising methane, a C2-6 alkene and optionally a C2-6 carboxylic acid.

2. The process according to claim 1, wherein the volume ratio of methane to the C2-6 alkane is of from 0.005:1 to 4.8:1.

3. The process according to claim 1, wherein C2-6 alkene is converted into another chemical product.

4. The process according to claim 3, wherein the C2-6 alkane is ethane and the C2-6 alkene is ethylene, which ethylene is converted into ethylene oxide.

5. The process according to claim 4, comprising
   subjecting a stream comprising methane and ethane, in which stream the volume ratio of methane to ethane is of from 0.005:1 to 100:1 to oxydehydrogenation conditions resulting in a stream comprising methane, ethylene and optionally acetic acid;
   subjecting ethylene and methane from the stream comprising methane, ethylene and optionally acetic acid to oxidation conditions resulting in a stream comprising ethylene oxide and methane; and
   recovering ethylene oxide from the stream comprising ethylene oxide and methane.

\* \* \* \* \*